United States Patent [19]

Mullin et al.

[11] 4,105,702

[45] Aug. 8, 1978

[54] METHOD FOR PREPARING HALOGENATED ALKANES AND ALKENES

[75] Inventors: Charles R. Mullin, Sault St. Marie, Mich.; Donald J. Perettie, Lake Jackson, Tex.

[73] Assignee: The Dow Chemical Company, Midland, Mich.

[21] Appl. No.: 769,483

[22] Filed: Feb. 23, 1977

Related U.S. Application Data

[60] Continuation-in-part of Ser. No. 309,418, Nov. 24, 1972, abandoned, which is a division of Ser. No. 807,116, Mar. 13, 1969, Pat. No. 3,726,932.

[51] Int. Cl.$^2$ ............................................... C07C 17/00
[52] U.S. Cl. ........................... 260/658 R; 260/654 R
[58] Field of Search ........... 260/654 R, 658 R, 656 R, 260/664

[56] References Cited

U.S. PATENT DOCUMENTS

| | | | |
|---|---|---|---|
| 2,857,438 | 10/1958 | Obrecht et al. | 260/654 |
| 2,979,541 | 4/1961 | Pitt et al. | 260/654 |

*Primary Examiner*—Delbert E. Gantz
*Assistant Examiner*—Joseph A. Boska
*Attorney, Agent, or Firm*—Glwynn R. Baker

[57] ABSTRACT

A method for preparing halogenated alkanes and alkenes which comprises reacting by contacting, for 0.005 to 0.1 second at a temperature of 675° C to 850° C, a halogenating agent of the formula $CCl_xBr_{4-x}$, wherein $x$ is an integer from 0 to 4, with a compound of the formula $R_2CH_2$, wherein each R is H, Cl or Br, with or without the presence of inert gases. The utilization of the above conditions prevents the formation of large amounts of undesirable tars.

3 Claims, No Drawings

METHOD FOR PREPARING HALOGENATED ALKANES AND ALKENES

CROSS-REFERENCE TO RELATED APPLICATIONS

This is a continuation-in-part of our copending application Ser. No. 309,418 filed Nov. 24, 1974, now abandoned, which is a division of application Ser. No. 807,116 filed Mar. 13, 1969, now U.S. Pat. No. 3,726,932.

BACKGROUND OF THE INVENTION

U.S. Pat. No. 2,979,541 (Pitt et al.) teaches the reaction of $CCl_4 + CH_4$, at a temperature of 400° C to 650° C, for a residence time of 0.1 seconds to 20 seconds.

Said process produces low yields of useful chlorinated alkanes and alkenes, and produces large amounts of undesirable tars, i.e., hexachloroethane and other high boiling materials, which can clog the reactor and are difficult to separate from the desired product.

SUMMARY OF THE INVENTION

The present invention is a method for preparing halogenated alkanes and alkenes which comprises reacting by contacting, for 0.005 to 0.1 seconds at a temperature of from about 675° C, a halogenating agent of the formula $CCl_xBr_{4-x}$, wherein $x$ is an integer from 0 to 4, with a compound of the formula $R_2CH_2$, wherein each R is H, Cl or Br. An inert gas such as nitrogen, argon, krypton or neon can be employed as a diluent to improve the yield of 1,1,2-trichloroethylene if such is desired.

The utilization of the above method results in high yields of valuable halogenated compounds without the usual undesirable side effect of the formation of large amounts of tar.

The halogenating agents contemplated by this invention are $CCl_4$, $CCl_3Br$, $CCl_2Br_2$, $CClBr_3$ and $CBr_4$. The compounds to be halogenated are $CH_4$, $CH_3Br$, $CH_3Cl$, $CH_2Cl_2$, $CH_2Br_2$ and $CH_2ClBr$.

Compounds produced by the method of this invention include methyl chloride and bromide, vinylidene chloride and bromide, vinyl chloride and bromide, methylene, chloride and bromide, trichloroethylene, tribromoethylene, chloroform, bromoform and ethylene dichloride and dibromide.

Temperatures of from 675° C to 850° C are suitable for the method of this invention. For the reaction of $CCl_4 + CH_4$, a temperature of 730° C to 770° C is preferred, while for the reaction of $CCl_4 + CH_3Cl$, a temperature of 740° C to 800° C is preferred.

Inert diluents (N), such as nitrogen, argon, krypton or neon can be utilized in amounts of from 1 to 98 moles inert per mole of $RCH_2$ to produce mole ratios of $RCH_2 + N/CCl_xBr_{4-x}$ of from 10 to 100/1 and from at least 2/1 to 100/1 when nitrogen is absent. In the reaction of $CCl_4 + CH_3Cl$, for example, it has been found that by diluting the reactants with nitrogen in a mole ratio of about 10/1, the yields of $CHCl=CCl_2$ can be somewhat increased, with a resulting decrease in tar formation.

It is to be noted that excessive reaction times, i.e., above 0.1 second, greatly contribute to the formation of large amounts of undesirable tars. Therefore, it is important to observe the maximum contact times taught herein. Contact times ranging from about 0.005 to about 0.1 second are suitable. For the reaction of $CCl_4 + CH_4$, a contact time of about 0.02 to 0.04 second is preferred, while for the reaction of $CCl_4 + CH_3Cl$, a contact time of about 0.01 to 0.04 second is preferred.

In the reaction of $CCl_4 + CH_4$, the mole ratio of $CH_4/CCl_4$ is preferably about 60 to 90/1; in the reaction of $CCl_4 + CH_3Cl$, the mole ratio of $CH_3Cl/CCl_4$ is at least about 2/1, and more preferably about 3/1. In the reaction $CCl_4 + CH_3Cl$, an inert diluent (N), such as nitrogen, may be added to increase the overall mole ratio of $(CH_3Cl + N)/CCl_4$ to about 10/1 to 100/1.

Pressure has not been found to be critical, and can suitably vary from subatmospheric to superatmospheric. Experimentation has also shown that the results of the reactions were independent of the material of construction of the reactor and the conditioning of same, i.e., smooth or rough interior walls.

SPECIFIC EMBODIMENTS

EXAMPLE 1

$CH_4$ was mixed with $CCl_4$ and passed into a preheater (100° C – 300° C). The mixture was then passed into a Monel reactor (3 mm I.D. by 21 inches long). The effluent was analyzed by vapor phase chromatography (V.P.C.). Less volatile products were trapped in a dry ice-methylene chloride trap, and also analyzed by V.P.C. The temperatures reported in Table I below are accurate for approximately 90 percent of the length of the tube. The reactor temperature was monitored with thermocouples spaced one inch apart along the entire length of the reactor.

TABLE I

| Temp. (° C.) | $CH_4/CCl_4$ Mole Ratio | $CCl_4$ Feed (cc/sec.) | $CH_4$ Feed (cc/sec.) | Diluent Feed (cc/sec.) | Contact Time (sec.) | $CCl_4$ Conv. | Tar | Mole % $CH_2=CCl_2$ | $CHCl_3$ | $CH_3Cl$ |
|---|---|---|---|---|---|---|---|---|---|---|
| 718° | 78 | 0.92 | 71.4 | 0 | 0.037 | 30 | 0 | 60 | 20 | 20 |
| 725° | 78 | 0.70 | 54.8 | 0 | 0.047 | 61 | 0 | 45 | 21 | 21 |
| 745° | 78 | 0.92 | 71.4 | 0 | 0.037 | 51 | 0 | 70 | 15 | 15 |
| 770° | 78 | 0.92 | 71.4 | 0 | 0.037 | 75 | 0 | 70 | 12.5 | 12.5 |

Feed rates are given, and contact times were calculated by utilizing the volumetric flow rate in the reaction zone (total reactor volume) at the specific reaction temperature, assuming ideal gas conditions.

Conversion and product distribution are in mole percent. The product distributions quoted are calculated on the basis of one mole of $CCl_4$ reacted. The HCl present in the product is not calculated since other products account for its presence in an absolute sense. Where material balance is lacking, $CCl_2=CCl_2$ accounts for the remainder.

EXAMPLE 2

$CH_3Cl$ was mixed with $CCl_4$ and passed into a preheater (100° C to 300° C). The mixture was then passed into a 2 foot long × 3 mm I.D. Monel capillary tube heated externally by a resistance tube furnace. The effluent was analyzed by the same techniques as described in Example 1.

The temperatures reported in Table II below are accurate for approximately 80 percent of the length of the tube. Temperature was measured by inserting a thermocouple in the reactor and taking temperature measurements along the length of the tube. Feed rates are given, and contact times were calculated by the same technique as used in Example 1.

TABLE II

| Temp. °C. | mole ratio $CH_3Cl/CCl_4$ | Feed (cc/sec.) | $N_2$+ $CH_3Cl$- Feed (cc/sec.) | Time (sec) | $CCl_4$ conv. | $CH_2$- $CCl_2$ | $CH_2$- $Cl_2$ | $CHCl=CCl_2$ | Mole % $CH_2Cl$- $CH_2Cl$ | $CH$- $Cl_3$ | $CCl_2=CCl_2$ | $CHCl=CH_2$ | Tar |
|---|---|---|---|---|---|---|---|---|---|---|---|---|---|
| 800° | 3 | 0.50 | 9.5 | 0.017 | 28 | 26.0 | 11.0 | 41 | 8.0 | 9.0 | 6.5 | 0 | 0 |
| 800° | 3.4 | 0.50 | 9.5 | 0.024 | 36 | 21.0 | 7.0 | 34 | 9.0 | 8.0 | 4.0 | 5.5 | 12 |
| 740° | 18 | 0.25 | 4.3 | 0.037 | 21 | 9.5 | 11.5 | 20.0 | 15.5 | 20.0 | 0.0 | 9.0 | 14.5 |

Conversion and product distribution are in mole percent. The product distribution is calculated on the basis of one mole of $CCl_4$ reacted. The HCl present in the product is not calculated.

We claim:

1. A method for preparing halogenated alkanes and alkenes which comprises reacting, by contacting in the absence of or in the presence of an inert diluent N for 0.005 to 0.1 second at a temperature of from about 675° C to 850° C, a halogenating agent of the formula $CCl_xBr_{4-x}$, wherein $x$ is an integer from 0 to 4, with a compound of the formula $R_2CH_2$, wherein one R is H, Cl or Br and the other R is Cl or Br; and wherein the mole ratio of $R_2CH_2+N/CCl_xBr_{4-x}$ is from at least 2/1 to 100/1 when N is absent and from 10/1 to 100/1 when N is present.

2. The method of claim 1 wherein one R is H and the other is Cl, $x$ is 4, the temperature is 740° C to 800° C, and the contact time is 0.01 to 0.04 seconds.

3. The method of claim 2 wherein N is nitrogen and is utilized as an inert diluent in an amount such that the mole ratio $CH_3Cl + N/CCl_4$ is about 10/1 to 100/1.

* * * * *

UNITED STATES PATENT AND TRADEMARK OFFICE
CERTIFICATE OF CORRECTION

PATENT NO. : 4,105,702

DATED : August 8, 1978

INVENTOR(S) : Charles R. Mullin and Donald J. Perettie

It is certified that error appears in the above-identified patent and that said Letters Patent are hereby corrected as shown below:

Column 1, Line 8, delete "1974" and insert -- 1972 --.

Column 1, Line 27, after "675°C" insert -- to 850°C --.

Column 1, Line 53, delete the "," between "methylene and "chloride".

Column 2, lines 34-53, "The temperature . . . . . . . . . . . ideal gas conditions" is a new paragraph.

Columns 3 and 4, In the heading for Table II insert -- $CCl_4$ -- above "Feed in Column 3.

Signed and Sealed this

Sixth Day of March 1979

[SEAL]

Attest:

RUTH C. MASON
Attesting Officer

DONALD W. BANNER
Commissioner of Patents and Trademarks